United States Patent [19]

Aggelis et al.

[11] Patent Number: 6,107,548
[45] Date of Patent: Aug. 22, 2000

[54] **DNA SEQUENCES FROM MUSKMELON (*CUCUMIS MELO*) RELATED TO FRUIT RIPENING**

[75] Inventors: Alexandros Aggelis, Crete, Greece; Donald Grierson, Nottingham, United Kingdom; Isaac John, Ann Arbor, Mich.; Zoi Karvouni, Athens, Greece

[73] Assignee: Zeneca Limited, London, United Kingdom

[21] Appl. No.: 09/142,514

[22] PCT Filed: Mar. 24, 1997

[86] PCT No.: PCT/GB97/00824

§ 371 Date: Sep. 9, 1998

§ 102(e) Date: Sep. 9, 1998

[87] PCT Pub. No.: WO97/37023

PCT Pub. Date: Oct. 9, 1997

[30] Foreign Application Priority Data

Apr. 2, 1996 [GB] United Kingdom .................. 9606906

[51] Int. Cl.[7] .................. A01H 5/00; A01H 5/08; C12N 15/82
[52] U.S. Cl. .................. 800/298; 435/320.1; 536/23.6; 800/278
[58] Field of Search .................. 435/69.1, 320.1, 435/419, 468; 536/23.6; 800/278, 286, 298, 309

[56] References Cited

U.S. PATENT DOCUMENTS 5,744,364   4/1998   Bird et al. .................. 435/419

OTHER PUBLICATIONS

Stam M, et al. "The silence of genes in transgenic plants." Ann. Bot. 79: 3–12, 1997.

Koziel MG, et al. "Optimizing expression of transgenes with an emphasis on post–transcriptional events." Plant Mol. Biol. 32: 393–405, 1996.

Smith CJS, et al. "Antisense RNA inhibition of polygalacturonase gene expression in transgenic tomatoes." Nature 334: 724–726, Aug. 25, 1988.

*Primary Examiner*—Amy J. Nelson
*Attorney, Agent, or Firm*—Liza D. Hohenschutz

[57] ABSTRACT

The invention provides isolated DNA sequences related to fruit ripening from muskmelon (*Cucumis melo*) having SEQ ID NO: 1 and SEQ ID NO: 2, or having a sequence which encodes the amino acid sequence encoded by SEQ ID NO: 1 or SEQ ID NO: 2. Also provided are DNA constructs, genetically modified plants and fruits containing the foregoing sequences, and methods of preparing genetically modified plants.

10 Claims, 8 Drawing Sheets

```
1      .......MSLIGKLVSELEINAAAEKFYEIFK...DQCFQVPNITPRCIQ    40
              :|:|||:.|  |:|..|:|:|:|||    |  . .:|:|  . ::.
1      MAHQHTISGLVGKLITESEVNCNADKYYQIFKHHEDLPSAIPHIYT.SVK    49

41     QVEIHGTNWDGHGHGSIKSWYYTIDGKAEVFKERVEFHDDKLLIVLDGVG    90
       .|| |||..       |::|.|:|.::||:  ..||:...::|:.  |   :|::
50     AVEGHGTTS.....GCVKEWCYILEGKPLTVKEKTTYNDETRTINHNGIE    94

91     GDVFKNYKSFKPAYQFVPKDRNHCQAILSI.EYEKLHHGSPDPHKYIDLM   139
       |::::.:||.|  :.. .  ||...:.    :  .|  :|||::.:||  |  .|:..::
95     GGMMNDYKKFVATLVVKPKANGQGSIVTWIVDYEKINEDSPVPFDYLAFF   144

140    IGITNDIGSHIK...   151
          . .:|:.||:
145    QQNIEDLNSHLCASD   159
```

FIG. 4(A)

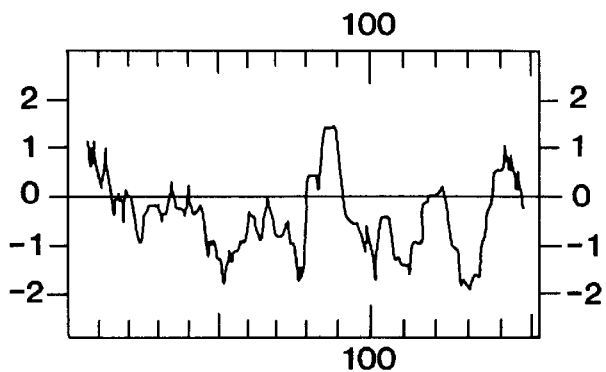

FIG. 4(B)

SEQUENCE LISTING

<160> NUMBER OF SEQ ID NOS: 4

<210> SEQ ID NO 1
<211> LENGTH: 1512
<212> TYPE: DNA
<213> ORGANISM: Cucumis melo

<400> SEQUENCE: 1

```
tcgacttctc ttttcacgta cgaaaatgcc aaccagaatt gattgcacca gcaaatccta      60
caccctatga atttaaacaa ctttctgatg tggatgatca acaaagctta aggcttcaat     120
tgccattcgt aaatatctat ccccataatc caagtttgga gggaagagat ccagtgaagg     180
taataaagga agcaattgga aaggcgttgg tgttctacta tcctttagca ggaagattga     240
gagaaggccc aggtagaaag cttttgttg aatgtacagg tgaaggaatc ttgtttattg      300
aagcggatgc agatgtgagc ttagaagaat tgggatac tcttccatat tcactttcaa       360
gcatgcagaa caatattata cataacgctt taaattctga tgaagtcctc aattctccat     420
tattgctcat tcaggtgaca cgactcaagt gtggaggttt catttttggt ctttgtttca     480
atcatactat ggcagatggt tttggtattg tccaattcat gaaggctaca gcggagatag     540
ctcgtggagc ttttgctcca tctatttac cagtatggca aagagctctc ttaaccgcaa     600
gagaccctcc cagaatcact tttcgccact atgaatacga ccaagtagtc gacatgaaga     660
gcggcctcat tccagtcaat agcaagatcg atcaattatt cttctttagc caacttcaaa     720
tctccaccct tcgccaaact ttgccagccc accttcacga ttgccccttcc ttcgaggtcc    780
tcactgccta tgtttggcgc ctccgtacca tagcccttca atttaagcca gaggaggaag    840
tgcggtttct ttgcgtaatg aatctacgct cgaagatcga cataccatta gggtattatg    900
gtaatgcggt agttgttcct gcagtaatca ccaccgctgc gaagctttgt gggaacccac    960
ttggttatgc tgtagacttg attaggaagg ccaaggctaa ggcaacgatg gagtacataa   1020
agtctacggt ggatcttatg gtgattaaag gacgacccta tttcactgta gttggatcat   1080
ttatgatgtc agacctaacg agaattgggg ttgaaaacgt ggactttgga tggggaaagg   1140
ccatttttgg aggacctaca accacagggg ccagaattac acgaggtttg gtaagctttt   1200
gtgtaccttt catgaataga aatggagaaa agggaactgc gttaagtcta tgcttgcctc   1260
ctccagccat ggaaagattt aggcaaatg ttcatgcctc gttgcaagtg aaacaagtgg    1320
ttgatgcagt tgatagccat atgcaaacta ttcaatctgc ttcgaaataa ataatattgt   1380
tgaaggtggg tctgagttga acgatgaaat aaataatatt atatatatag tcatatgtgt   1440
ggctttaaaa ttatatttgg agtaaattac gtataaaatt cccatcgaaa taagatttg    1500
ttttcatggt ca                                                       1512
```

<210> SEQ ID NO 2
<211> LENGTH: 686
<212> TYPE: DNA
<213> ORGANISM: Cucumis melo

<400> SEQUENCE: 2

```
tctatatcta gagatagaag gtttaaaatc atgtctctaa ttggaaagct tgtgagtgaa      60
ttagagatca atgcagctgc tgagaaattt tacgaaatat tcaaagatca atgttttcag     120
gttcccaata taaccccccag atgcattcaa caagttgaaa ttcatggtac taattgggat    180
ggaaatggac atggctctat caagtcttgg tattacacta ttgatggcaa ggcagaagtt     240
```

```
tttaaggaac gggtcgagtt tcacgatgat aaattgttga tagtcttgga tggagtggga      300
ggagatgtgt tcaaaaatta taaaagcttt aaaccagctt accaatttgt acctaaggat      360
cgtaaccatt gccaggcaat tctgagtata gagtatgaga acttcatca tgggtctcct      420 gatcctcata agtatattga cctcatgatt ggtatcacta acgacattgg atctcacatt      480
aaataagtat ttaatgtctg tcacattctc aagtgtggct tgttaatttg ttgtgggaaa      540
gttatatttt attttgaagt aattttcgtg tggttgatta tgtatctttg ctattttgct      600
tttatatttc aataagttat atggtttata taatattaca aagtaaataa aatccaagga      660
tcatcccttg tttatgtttc gttatt                                           686
```

<210> SEQ ID NO 3
<211> LENGTH: 151
<212> TYPE: PRT
<213> ORGANISM: Cucumis melo

<400> SEQUENCE: 3

```
Met Ser Leu Ile Gly Lys Leu Val Ser Glu Leu Glu Ile Asn Ala Ala
 1               5                  10                  15

Ala Glu Lys Phe Tyr Glu Ile Phe Lys Asp Gln Cys Phe Gln Val Pro
                20                  25                  30

Asn Ile Thr Pro Arg Cys Ile Gln Gln Val Glu Ile His Gly Thr Asn
            35                  40                  45

Trp Asp Gly His Gly His Gly Ser Ile Lys Ser Trp Tyr Tyr Thr Ile
        50                  55                  60

Asp Gly Lys Ala Glu Val Phe Lys Glu Arg Val Glu Phe His Asp Asp
65                  70                  75                  80

Lys Leu Leu Ile Val Leu Asp Gly Val Gly Asp Val Phe Lys Asn
                85                  90                  95

Tyr Lys Ser Phe Lys Pro Ala Tyr Gln Phe Val Pro Lys Asp Arg Asn
                100                 105                 110

His Cys Gln Ala Ile Leu Ser Ile Glu Tyr Glu Lys Leu His His Gly
            115                 120                 125

Ser Pro Asp Pro His Lys Tyr Ile Asp Leu Met Ile Gly Ile Thr Asn
        130                 135                 140

Asp Ile Gly Ser His Ile Lys
145                 150
```

<210> SEQ ID NO 4
<211> LENGTH: 159
<212> TYPE: PRT
<213> ORGANISM: Papaver somniferum

<400> SEQUENCE: 4

```
Met Ala His Gln His Thr Ile Ser Gly Leu Val Gly Lys Leu Ile Thr
 1               5                  10                  15

Glu Ser Glu Val Asn Cys Asn Ala Asp Lys Tyr Tyr Gln Ile Phe Lys
                20                  25                  30

His His Glu Asp Leu Pro Ser Ala Ile Pro His Ile Tyr Thr Ser Val
            35                  40                  45

Lys Ala Val Glu Gly His Gly Thr Thr Ser Gly Cys Val Lys Glu Trp
        50                  55                  60

Cys Tyr Ile Leu Glu Gly Lys Pro Leu Thr Val Lys Glu Lys Thr Thr
65                  70                  75                  80

Tyr Asn Asp Glu Thr Arg Thr Ile Asn His Asn Gly Ile Glu Gly Gly
```

-continued

```
                        85                      90                      95
Met Met Asn Asp Tyr Lys Lys Phe Val Ala Thr Leu Val Val Lys Pro
                100                 105                 110

Lys Ala Asn Gly Gln Gly Ser Ile Val Thr Trp Ile Val Asp Tyr Glu
        115                 120                 125

Lys Ile Asn Glu Asp Ser Pro Val Pro Phe Asp Tyr Leu Ala Phe Phe
    130                 135                 140

Gln Gln Asn Ile Glu Asp Leu Asn Ser His Leu Cys Ala Ser Asp
145                 150                 155
```

DNA SEQUENCES FROM MUSKMELON (*CUCUMIS MELO*) RELATED TO FRUIT RIPENING

FIELD OF THE INVENTION

This invention relates to DNAs produced by melon (*Cucumis melo* L.) during fruit ripening and the use of these DNAs to control the ripening process.

BACKGROUND OF THE INVENTION

Thus, this invention relates generally to the modification of a plant phenotype by the regulation of plant gene expression. More specifically it relates to the control of fruit ripening by control of one or more than one gene which is known to be implicated in that process.

Two principal methods for the control of expression are known. These are referred to in take art as "antisense downregulation" and "sensedownregulation" or "cosuppression". Both of these methods lead to an inhibition of expression of the target gene.

Overexpression is achieved by insertion of one or more than one extra copies of the selected gene. Other lesser used methods involve modification of the genetic control elements, the promoter and control sequences, to achieve greater or lesser expression of an inserted gene.

In antisense downregulation, a DNA which is complementary to all or part of the target gene is inserted into the genome in reverse orientation and without its translation initiation signal. The simplest theory is that such an antisense gene, which is transcribable but not translatable, produces mRNA which is complementary in sequence to mRNA product transcribed from the endogenous gene: that antisense mRNA then binds with the naturally produced "sense" mRNA to form a duplex which inhibits translation of the natural mRNA to protein. It is not necessary that the inserted antisense gene be equal in length to the endogenous gene sequence: a fragment is sufficient. The size of the fragment does not appear to be particularly important. Fragments as small as 40 or so nucleotides have been reported to obtain the inhibitory effect. However, it has to be said that fewer nucleotides may very well work: a greater number, up to the equivalent of full length, will certainly work. It is usual simply to use a fragment length for which there is a convenient restriction enzyme cleavage site somewhere downstream of fifty nucleotides. The fact that only a fragment of the gene is required means that not all of the gene need be sequenced. It also means that commonly a cDNA will suffice, obviating the need to isolate the full genomic sequence.

The antisense fragment does not have to be precisely the same as the endogenous complementary strand of the target gene. There simply has to be sufficient sequence similarity to achieve inhibition of the target gene. This is an important feature of antisense technology as it permits the use of a sequence which has been derived from one plant species to be effective in another and obviates the need to construct antisense vectors for each individual species of interest. Although sequences isolated from one species may be effective in another, it is not infrequent to find exceptions where the degree of sequence similarity between one species and the other is insufficient for the effect to be obtained. In such cases, it may be necessary to isolate the species-specific homologue. Antisense downregulation technology is well-established in the art. It is the subject of several textbooks and many hundreds of journal publications. The principal patent reference is European Patent No. 2540,208 in the name of Calgene Inc. There is no reason to doubt the operability of antisense technology. It is well-established, used routinely in laboratories around the world and products in which it is used are on the market. Both overexpression and downregulation are achieved by "sense" technology. If a full length copy of the target gene is inserted into the genome then a range of phenotypes is obtained, some overexpressing the target gene, some underexpressing. A population of plants produced by this method may then be screen and individual phenotypes isolated. As the antisense, the inserted sequence is lacking in a translation initiation signal. Another similarity with antisense is that the inserted sequence need not be a full length copy. Indeed, it has been found that the distribution of over- and under-expressing phenotypes is skewed in favour of underexpression and this is advantageous when gene inhibition is the desired effect. For overexpression, it is preferable that the inserted copy gene retain its translation initiation codon. The principal patent reference on cosuppression is European Patent No. 465,572 in the name of DNA Plant Technology Inc. There is no reason to doubt the operability of sense/cosuppression technology. It is well-established, used routinely in laboratories around the world and products in which it is used are on the market.

Sense and antisense gene regulation is reviewed by Bird and Ray in Biotechnology and Genetic Engineering Reviews 9:207–227 (1991). The use of these techniques to control selected genes in tomato has been described by Gray et al., Plant Molecular Biology, 19 69–87 (1992).

Gene control by any of the methods described requires insertion of the sense or antisense sequence, with appropriate promoters and termination sequences containing polyadenylation signals, into the genome of the target plant species by transformation, followed by regeneration of the transformants into whole plants. It is probably fair to say that transformation methods exist for most plant species or can be obtained by adaptation of available methods.

For dicotyledonous plants the most widely used method is Agrobacterium-mediated transformation. This is the best known, most widely studied and, therefore, best understood of all transformation methods. The rhizobacterium Agrobacterium tumefaciens, or the related Agrobacterium rhizogenes, contain plasmids which, in nature, cause the formation of disease symptoms, crown gall of hair root tumours, in plants which are infected by the bacterium. Part of the mechanism employed by Agrobacterium in pathogenesis is that a section of plasmid DNA which is bounded by right and left border regions is transferred stably into the genome of the infected plant. Therefore, if foreign DNA is inserted into the so-called "transfer" region (T-region)in substitution for the genes normally present therein, that foreign gene will be transferred into the plant genome. There are many hundreds of references in the journal literature, in text books and in patents and the methodology is well-established.

The effectiveness of Agrobacterium is restricted to the host range of the microorganism and is thus restricted more or less to dicotyledonous plant species. In general monocotyldonous species, which include the important cereal crops, are not amenable to transformation by the Agrobacterium method. Various methods for the direct insertion of DNA into the nucleus of monocot cells are known.

In the ballistic method, microparticles of dense material, usually gold or tungsten, are fired at high velocity at the target cells where they penetrate the cells, opening an aperture in the cell wall through which DNA may enter. The DNA may be coated on to the microparticles or may be added to the culture medium.

In microinjection, the DNA is inserted by injection into individual cells via an ultrafine hollow needle.

Another method, applicable to both monocots and dicots, involves creating a suspension of the target cells in a liquid, adding microscope needle-like material, such as silicon carbide or silicon nitride "whiskers" and agitating so that the cells and whiskers collide and DNA present in the liquid enters the cell.

In summary, the, the requirements for both sense and antisense technology are known and the methods by which the required sequences may be introduced are known. What remains, then is to identify genes whose regulation will be expected to have a desired effect, isolate them or isolate a fragment of sufficiently effective length, construct a chimeric gene in which the effective fragment is inserted between promoter and termination signals, and insert the construct into cells of the target plant species by transformation. Whole plants may then be regenerated from the transformed cells.

Fruit ripening is a complex developmental process which has been extensively used as a model system to dissect genetically programmed organ differentiation. Studies with both non climacteric and climacteric fruits such as apples, bananas, tomatoes, pears, avocados and mangos, have provided evidence for differential gene expression during ripening. Several enzymes showing altered activities during ripening have been reported and the respective genes have been cloned. The function of many ripening related genes is still unknown.

Muskmelon (*Cucumis mel* L.) is an economically important fruit that has an associated climacteric rise in ethylene production during ripening. Studies in melon, as with other climateric fruits, have shown that ripening is related to an increase in ethylene synthesis. A cDNA clone from melon with homology to the ACC-oxidase (Aco1) from tomato, which catalyst the terminal step in ethylene biosynthesis, has been isolated and shown to increase during ripening. The most notable physiological changes in fruit ripening are the softening of the mesocarp tissue, the accumulation of pigments, the development of the characteristic aroma and the sweet taste. Softening of the mesocarp is related to modification of pectin and hemicellulosic polysacharides. In melon, these changes are believed to be caused mainly by β-galactosidases, whereas polygalacturonase is important in tomato, avocado and pears. Other enzymes are also involved in cell-wall catabolism such as cellulase and xylanase. The change of colour in ripe fruits is usually due to carotenoid or anthocyanin accumulation and chlorophyll degradation. This has been studied in detail in tomato, which like melon, synthesises carotenoids during ripening. A cDNA clone with homology to tomato phytoene synthase, a key enzyme in the carotenoid pathway, has been isolated from melon and shown to be preferentially expressed during ripening. Sweetness is a characteristic attribute of ripe muskmelon and it is also used in quality evaluation. Sugar level appears to be regulated by the balance of invertases and synthases present in the fruit tissue. Ripe fruit aroma is associated with a mixture of over fifty compounds, some of which include thioesters. Production and release of aromatic volatiles are not well-understood. All these properties of the ripe fruit make it attractive to the consumer and their possible manipulation is scientifically and commercially interesting. There is, however, a need to identify additional genes involved in melon ripening.

SUMMARY OF THE INVENTION

This invention is concerned with the control of ripening in fruit and the particular interest here is in melons.

Our interest in controlling the ripening process is to improve the flavour and/or texture of fruit both characters being largely affected by the ripening process.

According to the present invention there is provided a ripening-related cDNA from melon, said DNA having the sequence SEQ ID NO 1 or SEQ ID NO 2 or a variant thereof which encodes the same polypeptide.

The invention further provides DNA coinstructs for the control of fruit ripening comprising promoter and termination regions operable in plant cells and therebetween a DNA having all or part of SEQ ID NO 1 or SEQ ID NO 2 in sense or antisense orientation.

Also, the invention provides a genetically modified plant having altered fruit ripening characteristics, said plant having stably incorporated in its genome a DNA construct comprising promoter and termination regions operable in plant cells and therebetween a DNA having all or part of SEQ ID NO 1 or SEQ ID NO 2 in sense or antisense orientation.

The invention also provides the fruit of the aforesaid genetically modified plant. Preferably the plant is melon. However, the invention also envisages the use of the melon-derived DNA of the invention to control the fruit ripening process in other fruit-producing plants.

BRIEF DESCRIPTION OF THE DRAWINGS

FIG. 4A shows the amino acid sequence encoded by the MEL7 cDNA clone and comparison with the major latex protein. FIG. 4A shows homology of the MEL7 polypeptide (upper sequence) (SEQ ID NO: 3) to the major latex protein of opium-poppy (bottom) (SEQ ID NO: 4). A period indicates a weak similarity, a colon indicates a strong similarity and a vertical line indicates identity of the compared amino acids. GAPS(. . .) were introduced to both sequences to optimise the alignment.

FIG. 4B shows a hydropathy plot of MEL7 predicted polypeptide. The hydropathy profile (window of 11 consecutive amino acids) was calculated according to Kyte and Doolittle (1982) and plotted against the amino acid number.

DETAILED DESCRIPTION OF THE INVENTION

Figure 1A:
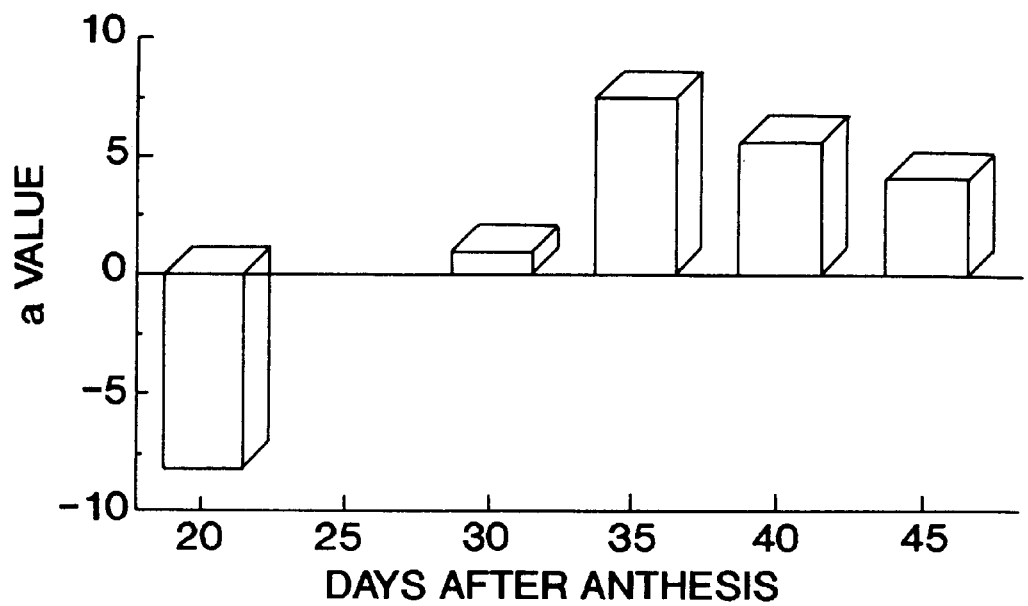
FIG. 1A shows changes in the color of melon fruits during ripening. The a hue component from the colour measurements was used, negative values indicate green and positive indicate red coloured fruits.

In our experimental work leading to this invention, we have used physiological and molecular approaches in this study. The period between 30 and 40 days after anthesis (daa) seemed to be the most active time in melon ripening although environmental factors such as temperature can affect the timing of ripening and the expression levels of some ripening-related genes. The colour of the flesh turned from green to orange and the mesocarp tissue started getting softer 30 daa. At this time aromatic compounds were released and the seeds were fully developed. Some of the changes in the fruit were correlated with the ethylene levels (FIG. 1). When ethylene evolved was measured from detached fruits, it was noticed that comparable ethylene levels were associated with fruits of similar physiological stage and appearance. The ethylene measurements in this report agree with the previous data of ethylene production in melon cultivars.

We have isolated two new ripening-related cDNAs designated as MEL2 and MEL7. The MEL2 mRNA was undetected in the early stages of ripening but it showed an enormous increase in expression between 30 daa and 40 daa. Its expression peaked at 40 daa when the fruit was ripe and then decreased. The MEL2 mRNA was detected only in the fruit and not in any other plant organ tested. The MEL7 mRNA was detected in various organs of the melon plant and in the early stages of ripening. It showed a significant increase in mRNA expression from 215 daa. The expression pattern of MEL7 mRNA during fruit ripening was similar to MEL2.

In melon fruits an increase in the amounts of mRNAs encoding enzymes involved in the ethylene biosynthesis pathway, such as ACC-oxidase, ACC-synthase and carotenoid production, including phytoene synthase, has been reported. Polyacrylamide gel electrophoresis of proteins synthesised in vitro using ripe and unripe melon fruit mRNA showed that several proteins increased in abundance during ripening. The 51 kD and 36 kD proteins may represent the ACC-synthase and ACC-oxidase respectively and the 43 kD protein might represent the phytoene synthase, since the molecular weights of these proteins correspond to those established for these enzymes. The protein of 17 kD that increased during ripening has the predicted size of the MEL7 polypeptide.

The presence of ethylene seems to play a role in regulating MEL2 AND MEL7 mRNA levels. After 48 hours in a high ethylene atmosphere MEL2 mRNA expression was induced and could be detected even in the 20 daa fruit. The MEL7 mRNA was also induced after 48 hours of ethylene treatment. Wounding of the tissue resulted in a decrease of the MEL2 and MEL7 mRNAs which might mean that wounding affects their turnover rate or the transcription of the respective genes.

Southern analysis data showed that at least four genomic EcoRV fragments hybridised to the MEL2 cDNA probe, showing that there are more than one corresponding genes for MEL2. The differences in the hybridising signal in digestions with EcoRV and SalI (FIG. 7A), might suggest that some genes have low homology at the nucleotide level. Since there is no internal EcoRV site in the MEL2 cDNA sequence, the detection of a 1.0 kb hybridising band suggests that the restriction site might be located in an intron sequence. There was only one genomic fragment which hybridising to the MEL7 cDNA probe, with approximate size of 33.6 kb, when melon genomic DNA was digested with EcoRI and BamHI enzymes. This result indicated that MEL7 might originate from a single or low-copy gene.

The RNA binding motif (RNP-CS1), the most conserved region identified as characteristic of RNA-binding proteins, was found in the MEL2 predicted polypeptide sequence. It is the first time that such a concensus sequence has been found in any ripening-related genes so far identified. Its presence indicated the possible involvement of this protein in the regulation of RNA turnover. It has been shown that nuclear-locating target signals function in plants but the absence of the N-terminal sequence makes it difficult to speculate about the localisation of the MEL2 protein and its possible regulatory role in transcription, pre-mRNA processing or translation of ripening-related gene(s). However, this could be clarified by immunolocalization of MEL2 protein in the fruit cells.

The homology of the MEL7 predicted polypeptide to the major latex protein is interesting. This is the main protein of latex fluid in opium-poppy Nessler et al., Plant Physiology 79, 499–504 (1985). Latex is produced especially in differentiated cells called laticifer cells and its presence has been reported in many plant families. The detection of the MEL7 mRNA in higher amounts in roots and stems than in other vegetative tissues coincides with the distribution of laticifer cells in plants. The dominant views about the function of latex are that it is involved in the sealing of wounds and the storage of secondary metabolites. It has been reported that ethylene can increase the production of latex and the activity of various enzymes in laticifer cells. If the MEL7 protein proves to be the melon counterpart of the major latex protein then its role might be in the protection of the ripe fruit against infection and wounding. This view is supported by the fact that the Sn-1 gene product was normally detected only in ripe bell pepper fruit but it could also accumulate in the green fruit 15 hours after wounding. It is known that fruits become more susceptible to infection and damage during ripening, probably because of the softening of the cell walls. It was assumed that the MEL7 expression would have been induced by wounding but our results showed that its mRNA levels dropped after wounding of the mesocarp tissue. This indicates that there is no general induction of this mRNA in response of wounding. It is possible, however, that the regulation and function of the protein vary in different cell and tissue types.

The accumulation pattern of mRNAs homologous to these clones suggests their possible role in melon ripening, for example, in RNA processing or turnover and wound sealing. Since the MEL2 mRNA is ripening-specific, the isolation if the MEL2 promoter will be very useful for genetic modification of melon.

The following is a description of the materials and methods employed in the Examples described hereinafter.

Plant Tissue

Melon seeds (*Cucumis melo* L. cv. Cantaloupe charentais) were provided by Tezier Breeding Institute, Velence, France and grown in a glasshouse in 5 liter pots under 16 hours of light. Freshly opened female flowers were hand-pollinated and tagged to identify fruit of known age. One fruit per plant was allowed to develop. Fruits were harvested after 15, 20, 25, 30, 35, 40 and 45 days after anthesis (daa). The ripening stage of fruit was also assessed by measuring the rate of ethylene evolution immediately after harvesting. The mesocarp tissue was separated from the seed cavity and epidermis, cut into small pieces, frozen in liquid nitrogen and stored at 70° C.

Ethylene measurements

Fruits were harvested and sealed in air-tight glass containers. They were incubated for 2 hours at room temperature and 1 ml of gas, withdrawn from the container via a Suba-seal, was used to quantify the external released ethylene, using a Pye Unicam PU4500 Gas chromatograph.

Colour and texture measurements

The fruits were cut longitudinally and the colour measurements were taken with a Chroma meter (Minolta CR-200) by placing the probe on the fruit flesh 1.5 cm below the epidermis. For the texture measurements a cylindrical sample of fruit tissue 2 cm in length and 15 mm diameter was removed using a metallic corkborer, starting from the epidermis inwards to the seed cavity. The cylinder was compressed with a 12 mm diameter probe against a metallic base. The required force was pitted against the deformation, till the sample collapsed, for each fruit, using a TA-XT2 Texture Analyser (Stable Micro Systems).

RNA extraction

Different methods were used for total RNA extraction according to the kind of tissue. Total RNA from fruit samples and ovaries was extracted using the method described by Smith et al, Planta 168:94–100(1986). For leaf, stem, petal and seed material, total RNA was extracted according to the procedure of Wadsworth et al., Anal. Blochem 172:279–283 and for root samples the method described by Dean et al, EMBO.J.4:3055–3061(1985) was used. Poly(A)$^+$ mRNA was isolated from fruit total RNA using the polyATract kit (Promega).

Differential screening

Replicate plaque lifts, approximately 30,000 pfu per 140 mm plate, were made of a dilution of the cDNA library. Lifts were carried out using Hybond-N$^+$ (Amersham) membranes as described by the manufacturer. Replicate filters were hybridised to single strand cDNA probes generated from 0.5 $\mu$g poly(A$^+$RNA either from unripe or ripe fruit using Moloney Murine Reverse transcriptase (Stratagene) and [α-$^{32}$P]dCTP (Amersham). Hybridisation conditions were according to the Hybond-N$^+$ protocol (Amersham). Clones were isolated on the basis of their ability for preferential hybridisation to probes. Primary isolates were put through second and third round screens using similar probes until plaque-pure clones were isolated.

Northern blots

Northern blot analysis was carried out as described by John et al, The Plant J. 7(3):483–490(1995). The membranes were then exposed for autoradiography at −70° C. using intensifying screens. In addition to autoradiography, signal intensity on the membranes was quantified directly using an AMBIS 4000 radioanalytical imaging detector and analyzed using AMIBIS QuantProbe version 4 software.

Genomic DNA extraction and Southern blots

Genomic DNA was extracted from young leaves according to the method of Bernatzky et al, Theor.App.Genet.72:314–321(1986). Approximately 10 $\mu$g of genomic DNA was digested with restriction enzymes overnight and separated by electrophoresis on a 0.8% agarose gel. The DNA was transferred to nylon membranes (Genescreen plus, Du Pont) according to the manufacturer's instructions. The membranes were then hybridised with labelled probes (as described for the northerns) at 42° C. and exposed on autoradiographic film at −70° C.

Radiolabelled probes

DNA probes were synthesised according to the random priming method. The plasmids (pMEL2 and pMEL7) were digested with EcoRI and XHOI to remove the cloned inserts which were then separated by agarose gel electrophoresis. The cDNA inserts from agarose gel were purified using GenecleanII (Bio101) kit and used as templates for random prime labelling.

DNA sequence analysis

Sequencing was performed by the dideoxy chain termination method using synthetic oligonucleotides as primers. The plasmid DNA for sequencing was isolated using Qiagen columns and sequenced with the Sequenase V.2.0 (UBS) and Taqtrack (Promega) sequencing kits. The DNA sequences data was analyzed using the University of Wisconsin Genetics Computer Group (GCG) and DNA Strider programs.

In vitro translation

For in vitro translation two $\mu$g of poly(A)$^+$ mRNA from unripe (15 and 200 daa) and ripe (35 and 40 daa) fruit was used as template in the TNT coupled what germ extract (Promega), labelled with $^{35}$S-methionine (Amersham).

Wounding and ethylene treatment of unripe fruits

Unripe fruits (20 daa) were wounded by cutting into very small pieces using a scalpel blade and frozen in liquid nitrogen after 2 and 6 hours. Control unwounded material from the same fruits was frozen immediately after harvesting. For ethylene treatment, unripe fruits were sealed for 48 hours in 20 $\mu$l l$^{-1}$ ethylene atmosphere inside air-tight glass containers. The containers were ventilated every ten hours to avoid low oxygen conditions, resealed and the ethylene concentration was restored.

EXAMPLE 1

Ripening and fruit attributes

Figure 1B:
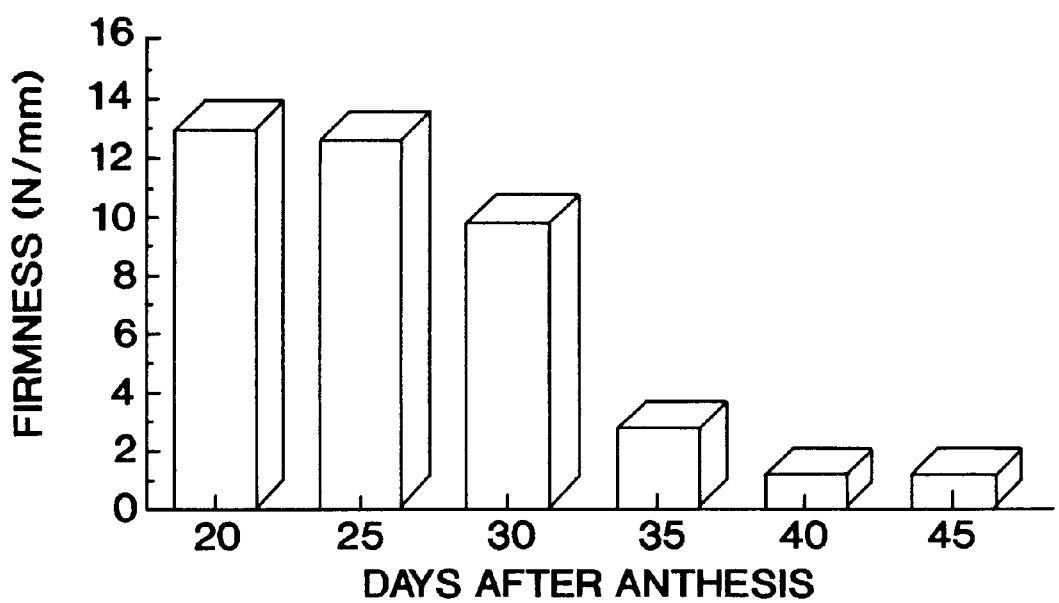
FIG. 1B shows the firmness of the fruit flesh expressed in Newton (N) per mm of deformation.
Figure 1C:
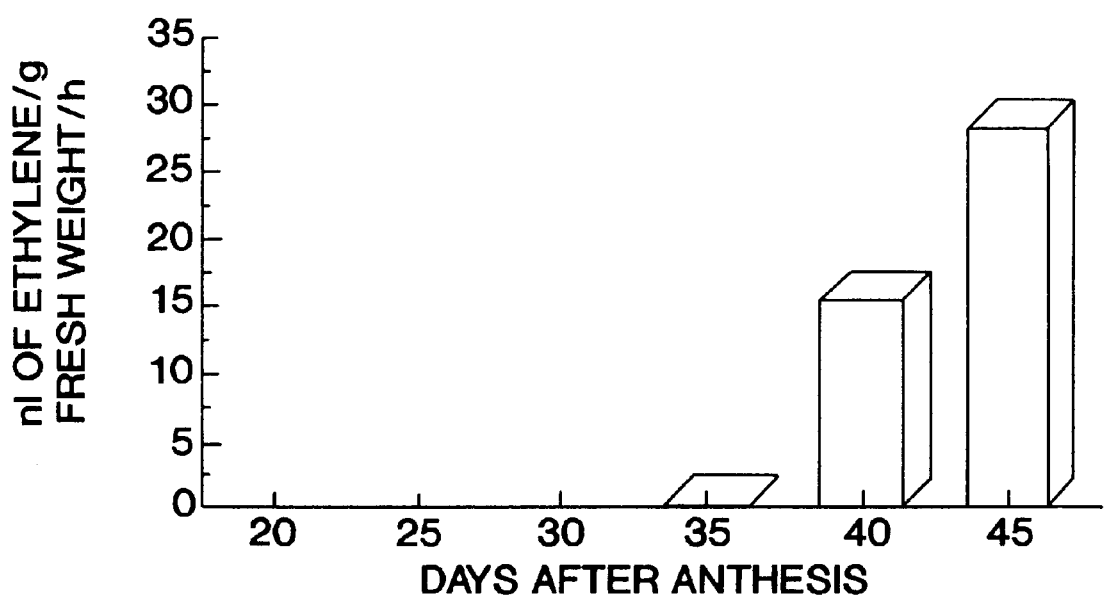
FIG. 1C shows the release of ethylene from the detached fruits. All the data were plotted against the age of the fruits from anthesis.

The change in melon flesh colour from green to characteristic orange started 30 days after anthesis (daa) (FIG. 1A) and was initially most obvious around the seed cavity. The change continued, spreading towards the epidermis till the final stage when the fruit reached a dark orange colour due to the accumulated pigments. The fruits also showed a dramatic decrease of firmness (force/deformation) between 30 and 40 daa (FIG. 1B). They started to soften 25 daa and became extremely soft and watery at 40 daa. The aroma of ripe melon was detectable 35 daa and increased till 45 daa. Ethylene from the ripening fruits was detectable at 35 daa which coincided with the time when the seeds were fully developed (FIG. 1C). It increased between 35 and 40 daa and then continued to increase at a slower rate till 45 daa. There was no ethylene detected from the green unripe fruits before 30 daa.

Changes in translatable mRNAs during ripening

Figure 2:
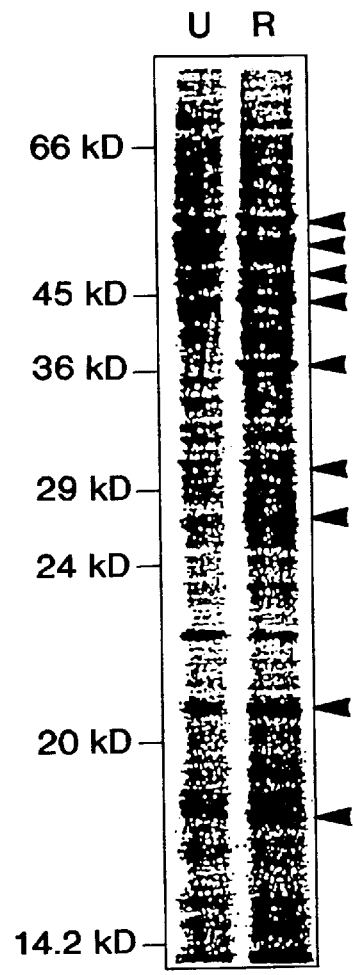
FIG. 2 shows changes in translatable mRNAs during ripening. In vitro translation products from unripe (U) and ripe (R) fruit poly(A)$^+$ mRNA were fractionated by SDS-PAGE. Proteins that increase in amount in the ripe fruit sample are indicated by arrowheads. The position of molecular weight markers are indicated on the left.

The in vitro translation products of poly(A)+ mRNA from ripe and unripe fruit revealed proteins that changed in abundance. Proteins with molecular weights of 55, 51, 47, 43, 36, 31, 27, 20 and 17 kD (FIG. 2) seemed to increase in the ripe fruit while there were some proteins that became undetectable as the fruit ripened. Similar changes were observed when the total proteins from different ripening stages were analyzed by SDS-PAGE (data not shown), although the molecular sizes of some proteins were different.

EXAMPLE 2

Isolation of MEL2 and MEL7 cDNA clones

Figure 3:
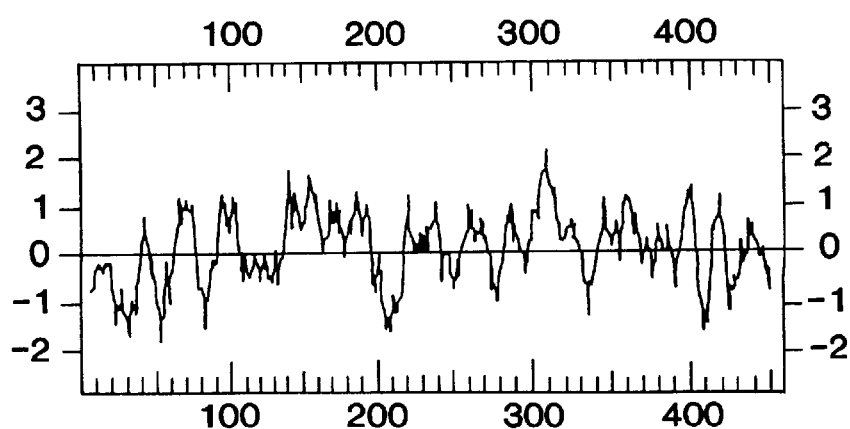
FIG. 3 shows a hydropathy plot of the MEL2 predicted polypeptide. The hydropathy profile (window of 11 consecutive amino acids) was calculated according to Kyte and Doolittle (1982) and plotted against the amino acid number.

Two cDNA clones showing differential expression were isolated from the melon ripe fruit cDNA library using single stranded cDNA probes from unripe and ripe fruit poly(A)+ mRNA. The MEL2 clone hybridised with a 1.6 kb transcript in ripening fruit RNA but the insert was 1512 bp, which indicates that it is not a full-length clone. It has an open reading frame (ORF) of 1370 nucleotides but lacks the initiation codon for the amino terminus. The 3' untranslated sequence is 142 bases in length and contains the putative polyadenylation signal. The predicted protein has three potential glycosylation sites and one RNA binding motif. Although the sequence is not complete the predicted protein has a high percentage (Leu 10.1%, Val 8.1%, Ile 6.2%, Ala 7.7%) of hydrophobic amino acids. Sequence analysis and hydropathy plot of the MEL2 predicted polypeptide (FIG. 3) did not reveal any signal peptide, although such a sequence if present might be in the missing 5' end of the clone. After sequence similarity search there was no significant homology with any of the known sequences in either nucleotide or protein data bases.

The MEL7 cDNA insert is 686 bp in length with an ORF of 456 nucleotides. A 200 bp untranslated sequence is present at the 3' end and has the putative polyadenylation signal at nucleotide position 646 to 651. Primer extension experiments showed that the MEL7 transcript is 14 bases longer than the cDNA (data not shown). The molecular weight of the predicted polypeptide is 17.3 kD with 151 amino acids (FIG. 4A). There is no signal peptide at the amino terminus of MEL7 and the hydropathy profile (FIG. 4B) shows no transmembrane regions in the polypeptide. There is one putative glycosylation site at position 33 to 35 of the amino acid sequence. The MEL7 polypeptide shows significant homology at the amino acid level with the major latex protein (33.5% identity and 61.6% similarity, FIG. 4A) isolated from opium-poppy (*Papaver somniferum*) and the predicted polypeptide of the Sn-1 gene (32.6% identity and 57.6% similarity) isolated from bell pepper (*Capsicum annuum*). All three polypeptides also have similar length and molecular weight.

EXAMPLE 3

Figure 5A:
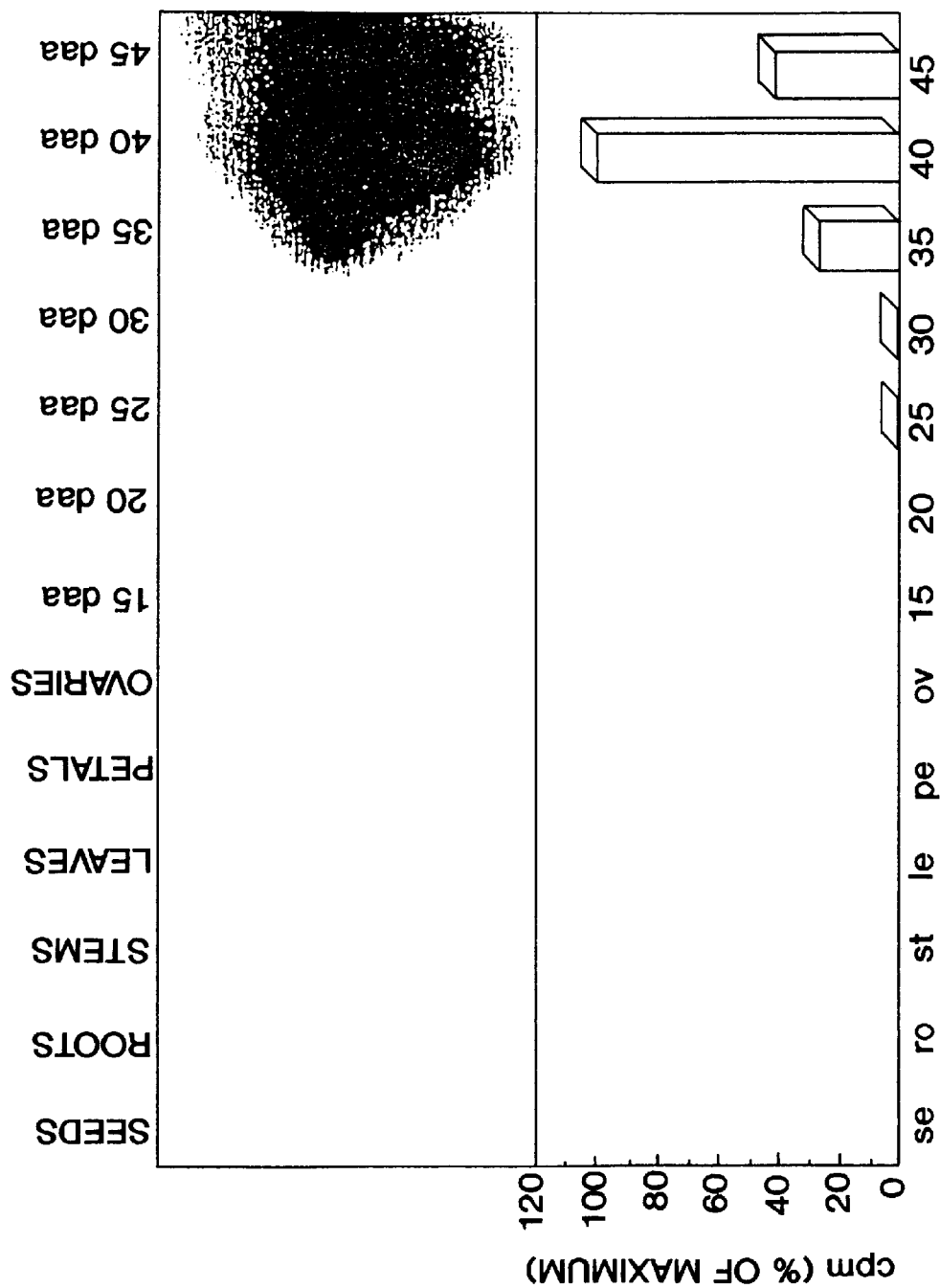
FIGS. 5A–5B show expression of MEL2 and MEL7 mRNAs, respectively, in melon organs and during fruit ripening. Total RNA from ripening stages and various organs of melon was electrophoresed in 1% agarose gels, blotted onto nylon membranes and hybridised with: MEL2 probe (FIG. 5A) and MEL7 probe (FIG. 5B). The MEL2 probed membrane was exposed for 12 hours while the membrane probed with MEL7 was exposed 18 hours for the fruit samples and 8 days for the other organ samples. The bottom panels show the quantification of the hybridisation of the membranes, expressed as a percentage of the maximum signal.
Figure 5B:
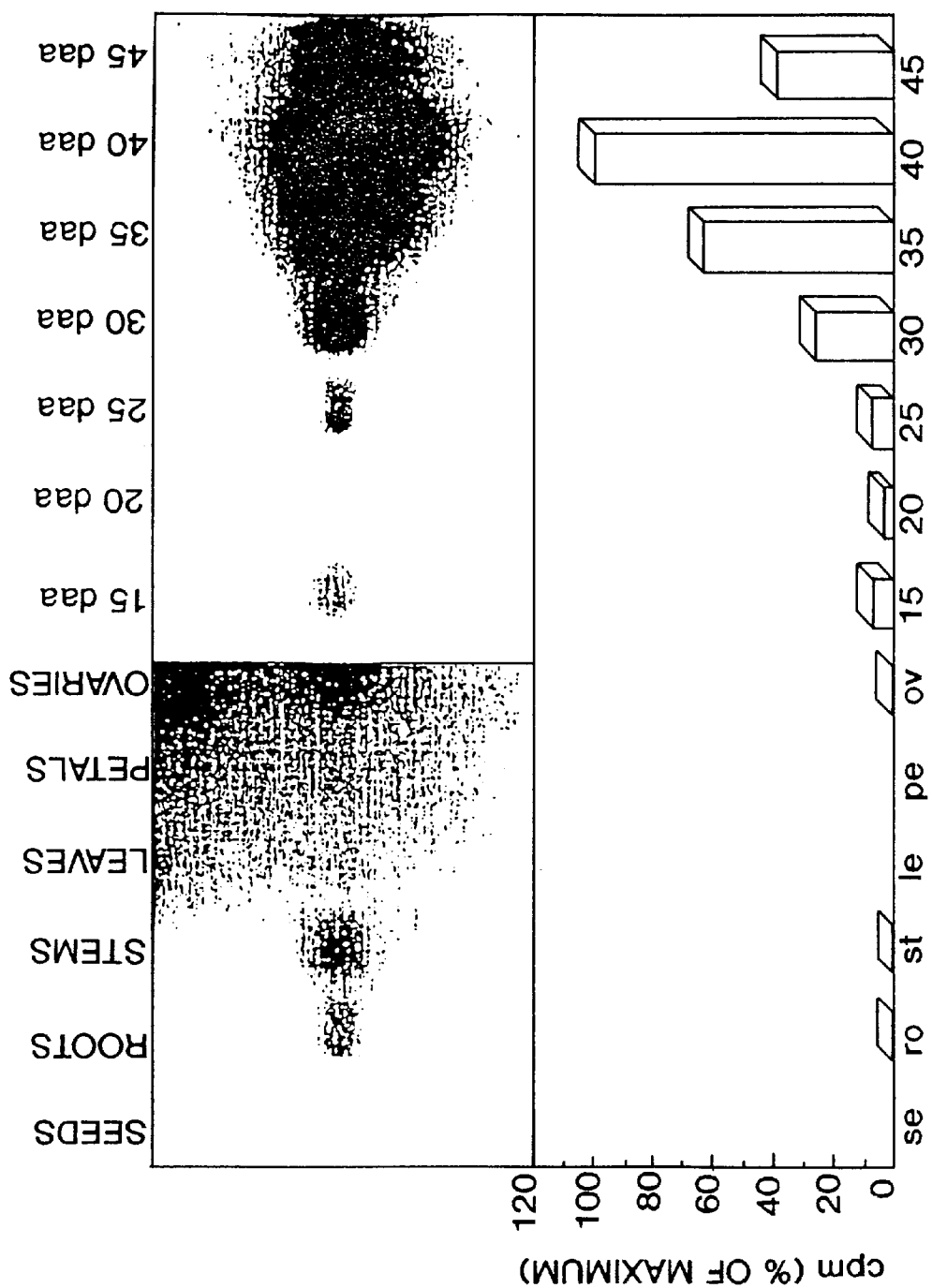

Expression of the MEL2 and MEL7 mRNAs during fruit development and ripening and in other organs Northern analysis using RNA from fruits and other organs of melon plants revealed that MEL2 mRNA accumulated only during ripening (FIG. 5A) and was not detected (less than 0.5% of maximum expression) in unripe fruits before 30 daa. The levels of MEL2 mRNA increased approximately 100-fold between 30 daa and 40 daa (FIG. 5A) and decreased 45 daa (approximately 40% of maximum), when the fruit became very soft and watery. The MEL2 mRNA was below the limit of detection in all other plant organs examined (FIG. 5A). The MEL7 mRNA was present in low amounts during the early stages of ripening, increased from 25 daa to 40 daa (13-fold) and then declined at 45 daa (approximately 40% of maximum) (FIG. 5B). The MEL7 mRNA was expressed in very small amounts in various other plant organs investigated and was slightly higher in roots (0.6% of maximum), stems (0.65% of maximum) and ovaries (0.57%) as compared to seeds, leaves and petals (note the longer exposure times for part of the autoradiograph in FIG. 5B). No MEL2 and MEL7 homologues were detectable when northern analysis of mRNA from tomato fruit using MEL2 and MEL7 as probes was performed under low stringency conditions of hybridisation and washings.

EXAMPLE 4

Expression of the MEL2 and MEL7 mRNAs after ethylene treatment and wounding

Figure 6A:
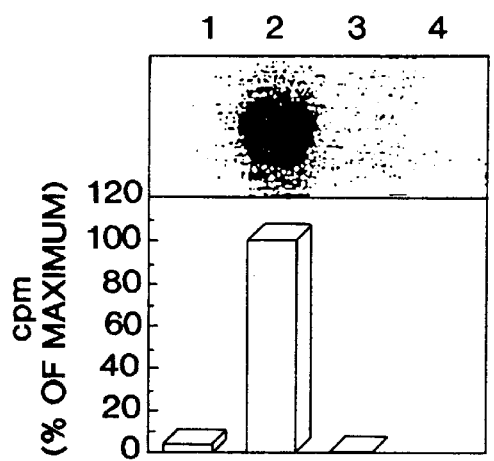
FIGS. 6A–6B show expression of MEL2 and MEL7 mRNAs in unripe melon fruits after ethylene treatment and wounding. Unripe melon fruits (20 daa) were treated with ethylene (20 $\mu$l-1$^{-1}$ for 48 hours) or wounded for two hours and six hours. The expression of MEL2 (FIG. 6A) and MEL7 (FIG. 6B) homologous mRNAs was determined using northern blot analysis. The RNA samples were: 1) Control untreated and unwounded fruit; 2) Ethylene treated fruit; 3) Wounded fruit after 2 hours; and 4) Wounded fruit after 6 hours. The accumulation of MEL2 and MEL7, determined by radioanalytical image detection of the northern blot membranes, is shown below the northern blot photographs. The results are expressed as a percentage of the maximum signal.

To examine the role of ethylene and wounding in the regulation of MEL2 and MEL7 genes, unripe fruits were incubated for 48 hours in a high (20 $\mu$l $1^{-1}$) ethylene atmosphere and also wounded. Northern analysis of the ethylene-treated and the wounded fruits revealed that MEL2 mRNA was undetectable in the 20 daa control fruit and was induced 27-fold after ethylene treatment. Wounding of the fruit tissue decreased the amount of MEL2 mRNA 7-fold, compared with the control, two hours after wounding and it became undetectable after six hours (FIG. 6A).

Figure 6B:
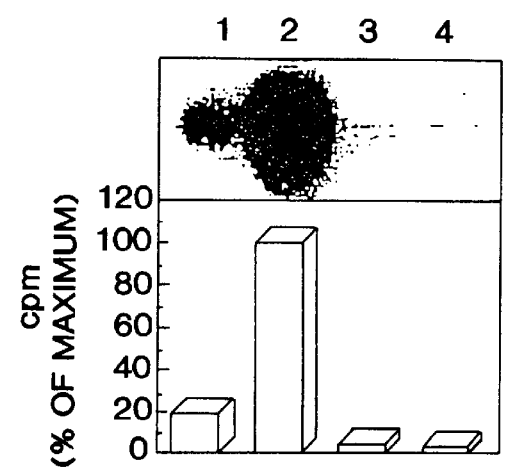

The MEL7 mRNA levels increased approximately 5-fold in response to ethylene when compared with the non-treated control samples. In wounded fruits there was more than an 80% decrease in MEL7 mRNA after two hours and approximately 95% decrease after six hours when compared with the control unwounded samples (FIG. 6B).

EXAMPLE 5

Genomic Southern analysis

Figure 7A:
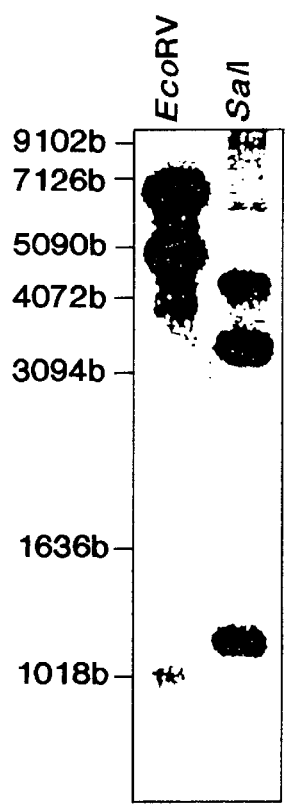
FIGS. 7A–7B show Southern analysis of MEL2 and MEL7 genes. Genomic DNA was isolated from melon leaves and digested with different restriction enzymes. The DNA was separated on a 0.8% agarose gel, transferred onto nylon membranes and probed with MEL2 (FIG. 7A) and MEL7 (FIG. 7B). Molecular weight markers are indicated on the left of each blot.

Melon genomic DNA was digested with several restriction enzymes and hybridised with MEL2 and MEL7 radiolabelled probes for southern analysis. Single digests of the genomic DNA generated hybridising bands with high molecular weight. To overcome this problem, double digests were also used. The MEL2 probe hybridised to four EcoRV fragments of approximately 6.5, 4.9, 3.8 and 1.0 kb and five SalI fragments of 9.0, 6.2, 4.3, 3.3 and 1.1 kb in size (FIG. 7A). In both lanes there were two classes of hybridising signals. The 6.5 and 4.9 kb bands in the EcoRV digest and the 4.3, 3.3 and 1.1 kb bands in the SalI digest gave very strong signal while the rest of the bands seemed to hybridise weakly. There is a single restriction site in the MEL2 cDNA sequence for the SalI enzyme at position 650 of the MEL2 cDNA sequence but none for the EcoRV enzyme.

Figure 7B:
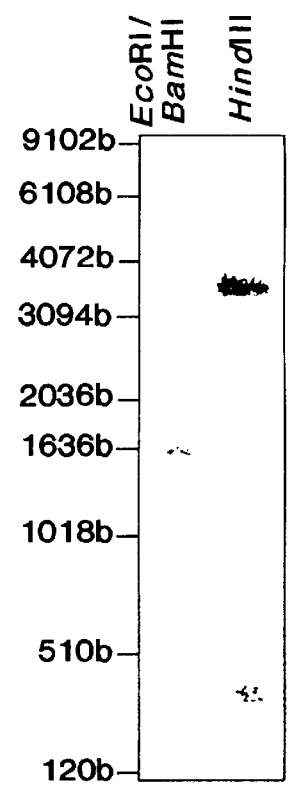

The MEL7 probe hybridised to a single 1.6 kb fragment when genomic DNA was digested with EcoRI and BamHI restriction enzymes. Neither EcoRI nor BamHI enzyme cuts the MEL7 cDNA insert. In the HindIII digest two fragments of 3.5 kb and 0.3 kb hybridised strongly with the MEL7 probe and two fragments with approximate size of 1.0 and 0.7 kb hybridised very weakly (FIG. 7B). The 0.3 kb fragment may be derived from the two internal HindIII restriction sites at positions 47 and 324 of the MEL7 cDNA sequence.

What is claimed is:

1. An isolated DNA comprising DNA having the sequence of SEQ ID NO: 1 or SEQ ID NO: 2, or having a sequence which encodes the amino acid sequence encoded by SEQ ID NO: 1 or SEQ ID NO: 2.

2. The DNA of claim 1 wherein said DNA comprises DNA having a sequence which encodes the amino acid sequence of SEQ ID NO: 3.

3. The DNA of claim 1 wherein said DNA comprises DNA having the sequence of SEQ ID NO: 1.

4. The DNA of claim 1 wherein said DNA comprises DNA having the sequence of SEQ ID NO: 2.

5. A DNA construct comprising promoter and termination regions operable in plants and therebetween the DNA as claimed in claim 1 wherein said promoter, said DNA and said termination region are operably linked.

6. A genetically modified plant having stably incorporated in its genome a DNA construct of claim 5.

7. The plant as claimed in claim 6 wherein said plant is a melon plant.

8. Fruit of the genetically modified plant as claimed in claim 6.

9. A method for the production of a genetically modified plant comprising
 (a) providing the DNA construct of claim 5;
 (b) inserting said DNA construct into a cell of a plant; and
 (c) regenerating a genetically modified plant from said cell.

10. A genetically modified plant produced by the method of claim 9.

* * * * *